United States Patent
Barrett et al.

(10) Patent No.: US 10,557,828 B2
(45) Date of Patent: Feb. 11, 2020

(54) ULTRASONIC PHASED ARRAY TRANSDUCER FOR THE NDE INSPECTION OF THE JET PUMP RISER WELDS AND WELDED ATTACHMENTS

(71) Applicant: Westinghouse Electric Company LLC, Cranberry Township, PA (US)

(72) Inventors: Charles R. Barrett, Ooltewah, TN (US); Kevin J. Foley, Chattanooga, TN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 1023 days.

(21) Appl. No.: 14/597,644

(22) Filed: Jan. 15, 2015

(65) Prior Publication Data
US 2015/0233869 A1    Aug. 20, 2015

Related U.S. Application Data

(60) Provisional application No. 61/940,581, filed on Feb. 17, 2014.

(51) Int. Cl.
*G01N 29/04* (2006.01)
*G21C 17/017* (2006.01)
*G01N 29/24* (2006.01)
*G01N 29/22* (2006.01)
(Continued)

(52) U.S. Cl.
CPC ......... *G01N 29/043* (2013.01); *G01N 29/221* (2013.01); *G01N 29/24* (2013.01); *G01N 29/262* (2013.01); *G21C 17/017* (2013.01); *G01N 2291/0234* (2013.01); *G01N 2291/044* (2013.01); *G01N 2291/106* (2013.01); *G01N 2291/267* (2013.01); *G21C 15/25* (2013.01)

(58) Field of Classification Search
CPC .. G01N 29/043; G01N 29/221; G01N 29/262; G21C 17/017
USPC ........................................................ 376/249
See application file for complete search history.

(56) References Cited

U.S. PATENT DOCUMENTS

| 4,149,420 A |   | 4/1979 | Hutchison et al. |
| 4,394,345 A | * | 7/1983 | De Briere ............ G01N 29/223 |
|             |   |        | 376/245 |
| 4,640,291 A |   | 2/1987 | 't Hoen |

(Continued)

FOREIGN PATENT DOCUMENTS

| JP | S54164182 | 12/1979 |
| JP | S5514862  | 1/1980  |

(Continued)

OTHER PUBLICATIONS

Westinghouse Electric Company LLC, PCT US2015/012423 International Search Report, dated Oct. 27, 2015, 11 pages.

(Continued)

*Primary Examiner* — Jack W Keith
*Assistant Examiner* — John T Nolan
(74) *Attorney, Agent, or Firm* — Joseph C. Spadacene; Westinghouse Electric Company LLC

(57) ABSTRACT

An ultrasonic phased array transducer assembly having a single housing in which a plurality of phased array transducer subassemblies are mounted at a skewed angle relative to a leading face of the housing and to each other, with each transducer mounted on composite wedge(s) at different orientations within the housing.

11 Claims, 5 Drawing Sheets

(51) Int. Cl.
    *G01N 29/26*     (2006.01)
    *G21C 15/25*     (2006.01)

(56)           References Cited

U.S. PATENT DOCUMENTS

| | | |
|---|---|---|
| 5,563,346 A | 10/1996 | Bartelt et al. |
| 2008/0178678 A1* | 7/2008 | Girndt .................... G01N 29/04 |
| | | 73/622 |
| 2012/0143063 A1 | 6/2012 | Robinson |
| 2013/0111995 A1 | 5/2013 | Koehler et al. |
| 2013/0199297 A1 | 8/2013 | Imbert et al. |
| 2013/0247350 A1 | 9/2013 | Specht et al. |

FOREIGN PATENT DOCUMENTS

| | | |
|---|---|---|
| JP | S58108453 | 6/1983 |
| JP | S6468652 | 3/1989 |
| JP | H11109081 | 4/1999 |
| JP | 2000-075080 A | 3/2000 |
| JP | 2013036770 | 2/2013 |

OTHER PUBLICATIONS

Westinghouse Electric Company LLC, EP15777243 Search Report, dated Aug. 28, 2017, 7 pages.

Masakazu Kamibayashi et al., "Study of Automatic Ultrasonic Testing Using Phased Array UT Techniques for Welded Joints (2nd Report, Development of Logic for Judigng Weld Defect, and Evaluation of Detectability)", Journal of JSNDI (The Japanese Society for Non-Destructive Inspection), (2009), No. 12, pp. 563-569, vol. 58.

\* cited by examiner

ULTRASONIC PHASED ARRAY TRANSDUCER FOR THE NDE INSPECTION OF THE JET PUMP RISER WELDS AND WELDED ATTACHMENTS

CROSS REFERENCE TO RELATED APPLICATION

This application claims priority to U.S. Provisional Patent Application Ser. No. 61/940,581, filed Feb. 17, 2014, entitled Ultrasonic Phased Array Transducer for the NDE Inspection of the Jet Pump Riser Welds and Welded Attachments.

BACKGROUND

1. Field

This invention relates generally to nondestructive examination transducers and, more particularly, to ultrasonic phased array transducers for inspecting components in restricted areas.

2. Related Art

A boiling water reactor (BWR) produces electrical power by heating water in a reactor pressure vessel that contains a nuclear fuel core in order to generate steam which is used to drive a steam turbine. Various components and structures in a nuclear reactor are examined periodically to assess their structural integrity and determine the need for repair. Ultrasonic inspection is a known technique for detecting cracks in nuclear reactor components. A number of the inspection areas in a nuclear reactor, such as a BWR, have limited access and, therefore, are difficult to assess using an inspection tool. A jet pump in a BWR is one such component.

The jet pump riser pipe welds are periodically inspected for cracking. The presence of cracking can diminish the structural integrity of the jet pump riser pipe and elbow; however, the jet pump riser pipe welds are difficult to access. Access to the jet pump riser pipe welds is limited to the annular space between the outside of the shroud and the inside of the reactor pressure vessel, between adjacent jet pumps. The ability to scan the pipe welds is additionally restricted within the narrow space between the jet pump riser pipe and vessel, shroud, or welded attachments such as the riser brace or restrainer brackets. The jet pump riser assembly is comprised of fillet welds in which attachments are welded to the riser pipe or butt welds in which elbows and pipes are amalgamated through welding.

Weldments including the weld and the heat affected zone adjacent to the weld are ultrasonically inspected, otherwise referred to as the "weld volume." Cracking orientation may be of two classifications; circumferential (parallel to the weld) or axial (perpendicular to the weld). The inspection of the weld volume for the detection of circumferential and axial orientated cracking is commonly performed by a combination of scans that involve transducer rotations or a combination of transducers positioned such that the ultrasonic sound beam(s) interrogates the weldment's heat affected zone in multiple directions (clockwise, counterclockwise and perpendicular to the weld).

Ultrasonic testing is a method of characterizing the internal structure of a test piece through the use of high frequency sound waves. The frequencies used for ultrasonic testing are many times higher than the limit of human hearing, most commonly in the range from 500 KHz to 20 MHz. High frequency sound waves are directional, and can travel through a steel medium until the beam strikes a boundary from another medium (such as a crack or void), at which point the beam is reflected back to be characterized.

Previous ultrasonic weldment inspection technology typically employed a single or dual element piezoelectric crystal transducer that generates a single beam on a specified wedge to create a predetermined angle in which the beam would travel through the medium. Multiple probes would be necessary to examine the weld volume in varying directions, angles or require the complexity of remote tooling for individual transducer rotation. Phased array probes utilized for weld inspections are advantageous as fewer transducers are needed, and more importantly they require less transducer manipulation. Phased array transducers have the advantage of being able to generate numerous ultrasonic beams from a single transducer assembly containing a row or rows of sensor elements in which each can be pulsed separately creating a single beam or multiple beams at various angles (array) in a sweeping manner in a first direction. Some phased array technology enables the transducers to steer the beam(s) generation in a second direction without rotation of the phased array transducer. The phased array sweeping and steering capabilities are driven by an ultrasonic operating system, the number of piezoelectric elements and the element's positioning within the housing.

Inspections using ultrasonic testing techniques can be difficult due to the complexity of the geometry of the object to be inspected or the limited access to the component. In such cases the transducer may be contoured to increase the coupling between the contact surface of the transducer and the component being inspected. Problems sometimes arise with the automated tooling that is used to maneuver the transducers and, more specifically, with the ability to maintain contact between the transducers and the component being examined. Maintaining contact between the flat surfaces of a transducer with the concave or convex surface of a pipe system can be challenging. Poor coupling may result in missed detection of a flaw or lack of data quality to satisfy the inspection requirements.

Furthermore, inspecting and repairing nuclear reactors, such as boiling water reactors, typically can require complex tooling in order to position or move the phased array transducer to complete the examination. Plant utilities have a desire to reduce the number of manipulator installations and removals to reduce radiological exposure as well as cost and plant outage impact. Tooling with less complexity typically has the advantage of added reliability and a smaller tooling design enables access to areas with limited proximities.

Accordingly, a new ultrasonic phased array transducer assembly is desired that is relatively small in size and uncomplicated.

Additionally, such a transducer is desired that requires less movement to fully interrogate a jet pump weld.

SUMMARY

These and other objects are achieved by an ultrasonic phased array transducer assembly having a single housing in which a plurality of phased array transducer subassemblies are mounted at skewed angles relative to a leading face of the housing and to each other, with each transducer mounted on a composite wedge within the housing. Preferably, the housing has a contoured face to substantially match the surface of a pipe to be inspected. Desirably, a conductor from each of the phased array transducers are tethered together into a single cable assembly which exits the housing at a single port. In one embodiment the housing has at least one mounting hole or shoulder for gimbal attachments.

The invention also contemplates a method of inspecting a jet pump riser pipe in a boiling water nuclear reactor with each riser pipe having at least one welded attachment such as a riser brace. The method positions at least one ultrasonic phased array probe assembly adjacent to the surface of the pipe wherein a front leading face of the probe assembly is positioned adjacent to a weld or weld volume to be inspected. The method then scans the jet pump riser with at least one ultrasonic phased array probe so that the scanned volume of the ultrasonic beam comprises an area extending from the weld down the pipe and extends from the scan surface down at least partially towards the opposing surface of the pipe. The ultrasonic phased array probe assembly contains at least two independent phased array transducers mounted on composite wedges and set at skewed angles relative to each other and the front leading face of the probe assembly. Preferably, the scanning angles are capable of detecting flaws oriented axially and circumferentially relative to the pipe welds without rotating the probe assembly.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
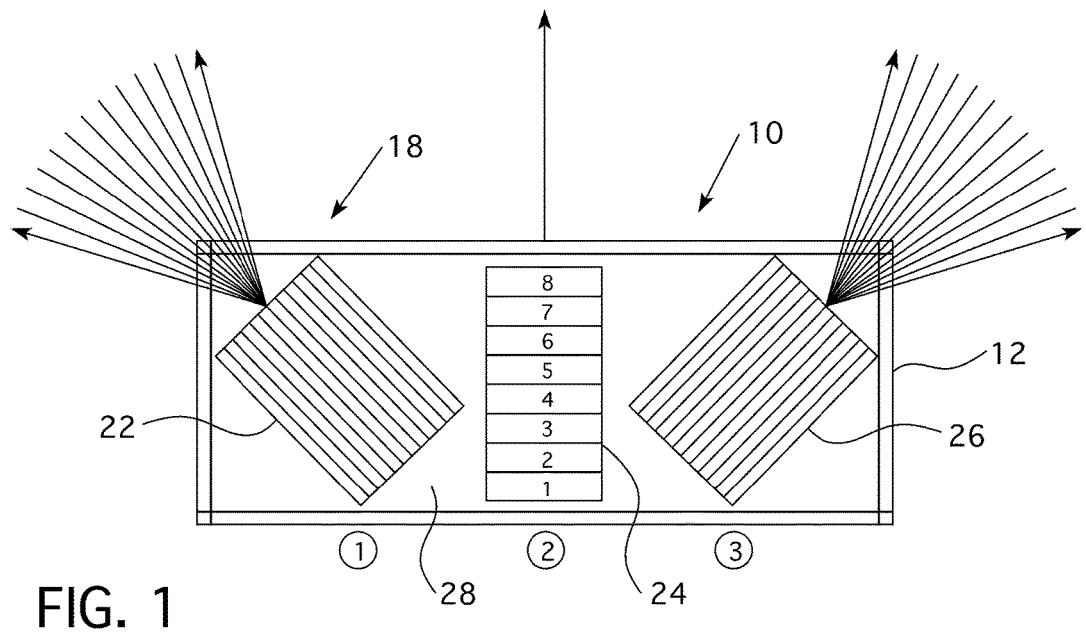
FIG. 1 is a schematic view of one embodiment of the ultrasonic phased array transducer assembly, including element position, of this invention.
Figure 2:
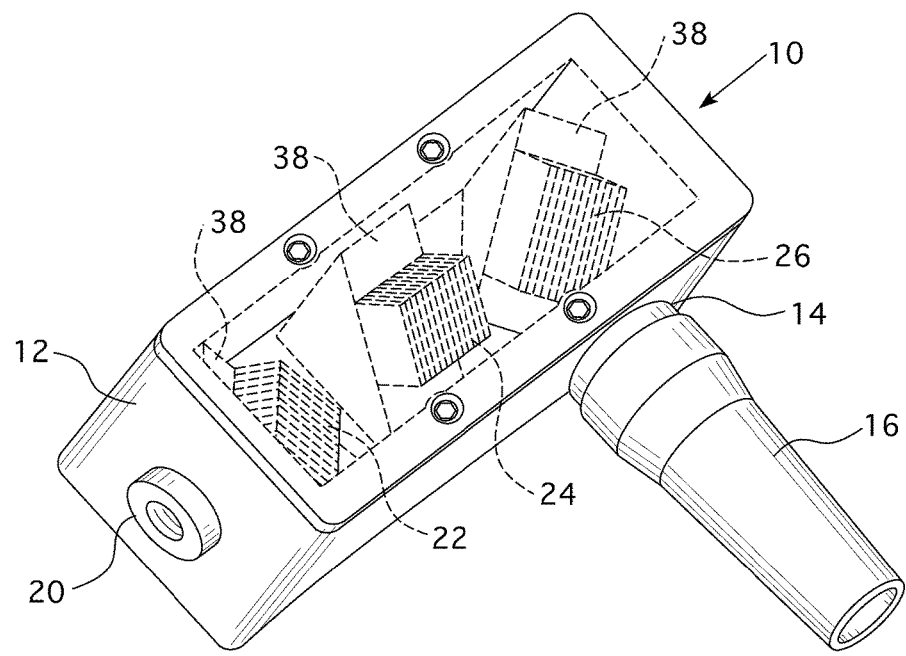
FIG. 2 is a top perspective view of the housing of the transducer assembly of FIG. 1.
Figure 3:
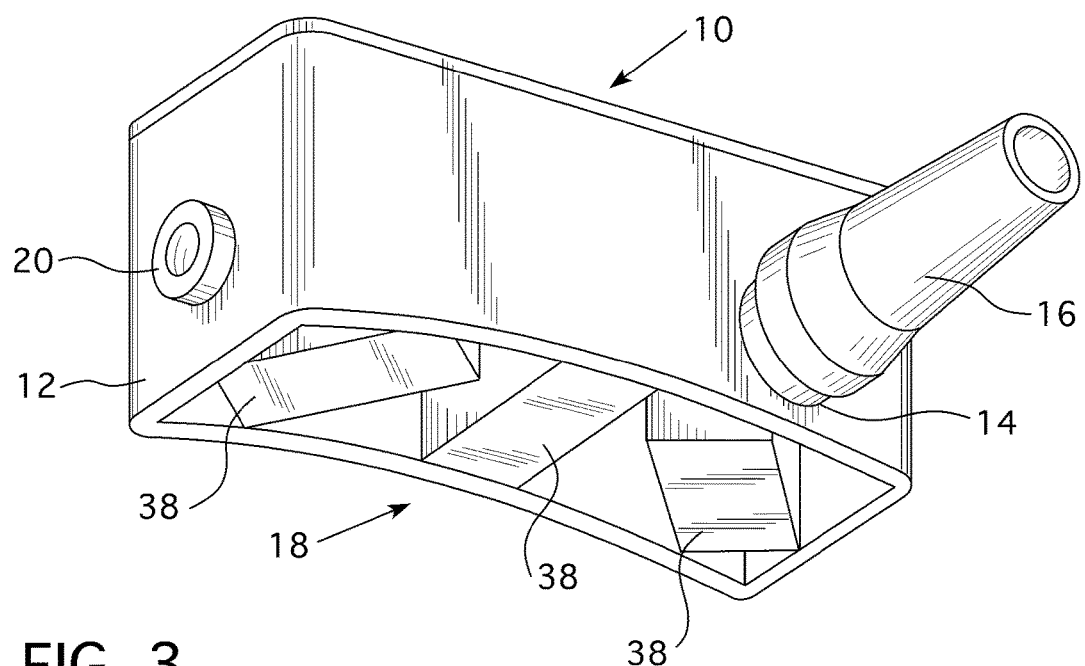
FIG. 3 is a perspective view of the housing of the transducer assembly of FIG. 1.

As can be seen in FIGS. 1-6, the phase array transducer assembly 10 of this invention contemplates a single housing 12 containing at least two independent phased array transducers utilized for the ultrasonic inspection of a jet pump riser pipe and associated riser pipe attachment welds in a boiling water reactor. An advantage of a single housing containing multiple phased array transducer subassemblies mounted in different positions and angles, whose outputs are coordinated, but independently controlled, is that such a design would eliminate the need to utilize multiple probes for the detection of various flaws which may differ in their orientation. This invention allows the number of tool reconfigurations, and the number of tools and/or probes required to perform inspections to be minimized. Further, when scanning on a contoured surface such as a pipe 36, the phased array transducer assembly 10 must have a contoured surface 18 to maintain a fixed sound path distance from the transducer elements within each of the subassemblies to the area to be inspected. This requirement further explains the desire to minimize the number of custom transducer housings that are needed to be employed for a weld inspection. In addition, due to the unique placement and orientation of the phased array subassemblies 22, 24, and 26, a compact overall housing 12 can be fabricated which allows maximum access to the weld around adjacent obstructions in the surrounding areas. The housing 12 includes a side wall and an opposing second side wall, an end wall and an opposing face 38. The side walls, the end wall and the face define a housing cavity 28 in which the phased array transducers are mounted.

Phased array transducers contain a row or multiple rows of elements referred to as the phased array subassembly that establish the parameters of the ultrasonic sound beam's steering or sweeping capabilities. Phased array transducer housings typically contain phased array subassemblies that are mounted on individual wedges which classically function in unity with one another to generate the desired beams. A more detailed understanding of the operation of ultrasonic phased array transducers can be found in U.S. Pat. Nos. 4,149,420 and 5,563,346. The novel probe assembly 10 of this invention utilizes phased array subassemblies 22, 24 and 26 mounted on separate wedges 38 positioned at dissimilar orientations within the housing, functioning as independent transducers and is not reliant on a plural wedge combination to generate the desired ultrasonic beams. Alternately, the phased array subassemblies may be mounted on a single piece of material with individual wedge surfaces machined to orient the subassemblies in their proper position.

Figure 5:
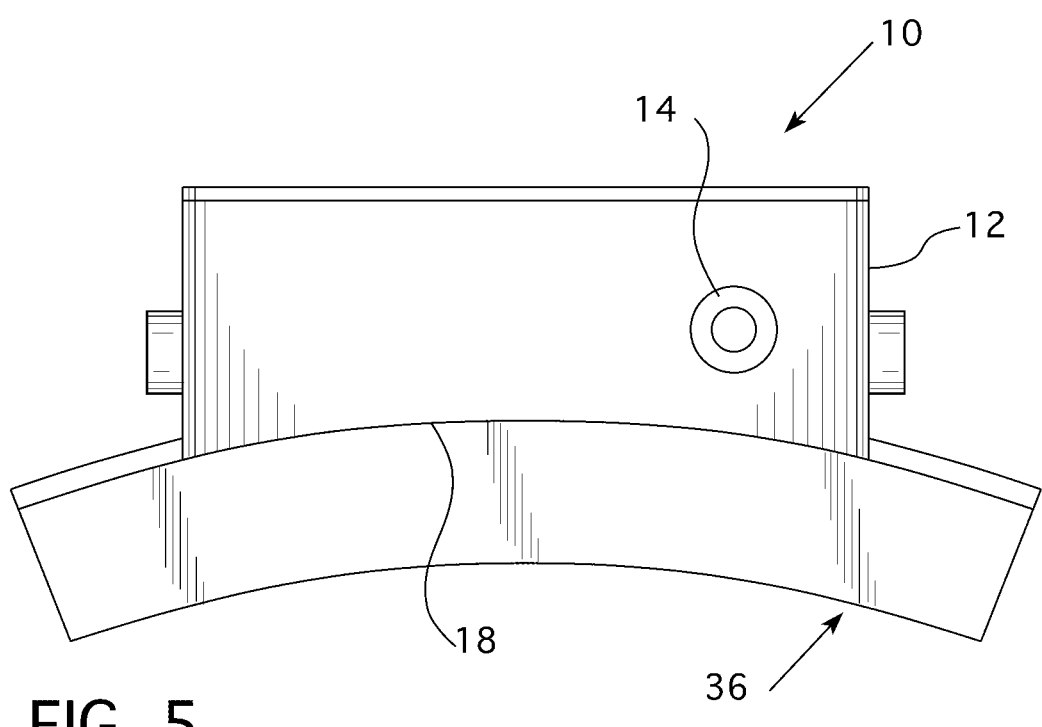
FIG. 5 is a rear view of the transducer assembly of FIG. 4 showing the curved face of the transducer housing similarly matching the curvature of the pipe.

The independent transducer conductors are tethered together in a joint cable 16 through a single port 14 in the housing 12. The port 14 is located such that it will not impede the face or front of the transducer from positioning at or near the weld toe. The housing 12 may contain shoulder mounts 20 for hardware gimbals on each side such that the face or front 18 of the transducer 10 can be positioned at or near a weld toe. The housing face 18 in contact with the surface of the jet pump piping 36 is a contoured such as to maximize coupling to the piping, as can be seen in FIG. 5.

Each transducer 22, 24 and 26, contained within the housing cavity 28 is fixed on at least one composite wedge 38 such as to generate at least one ultrasonic sound beam. The wedge 38 provides a means to set the transducer array at an angle relative to the inspection surface such that different elements of the array are fixed at different elevations relative to the inspection surface.

The transducer claimed herein has at least two phased array assemblies mounted at a skewed angle from each other and relative to the front leading edge 18 of the transducer housing 12. In one preferred embodiment, the single housing 12 contains three phased array transducers 22, 24 and 26. The center transducer 24 and the corresponding wedge is mounted such that its primary or center ultrasonic beam is directed in a plane perpendicular to the leading edge/face 18 of the housing 12. The two transducers 22 and 26 mounted on the clockwise and counter clockwise side of the centered transducer 24 are positioned inside the housing such that their primary or center ultrasonic beam is directed at an angle skewed from a plane perpendicular to the leading edge/face 18 of the housing 12, where the primary ultrasonic beams face away from each other, oriented approximately ninety degrees apart (at approximately reciprocal angles). Alternative configurations such as two, four, or more independent transducers can be utilized in a single housing 12 and would be considered to be within the concept claimed hereafter. In addition, alternative positions of each array may be utilized such that the array perpendicular to the leading edge/face is not the center array.

Figure 4:
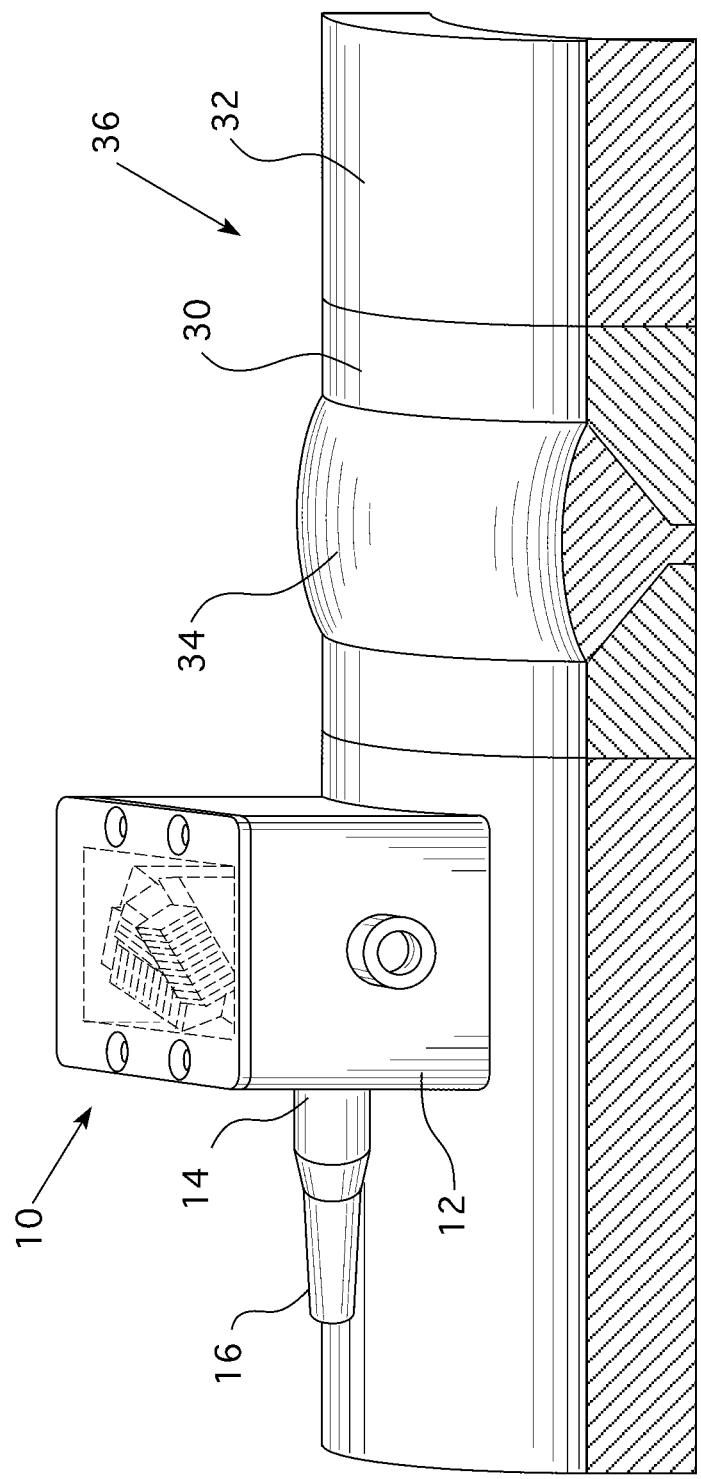
FIG. 4 is a schematic view of the transducer assembly of FIGS. 1, 2 and 3 positioned over a pipe adjacent a weld to be inspected.
Figure 6:
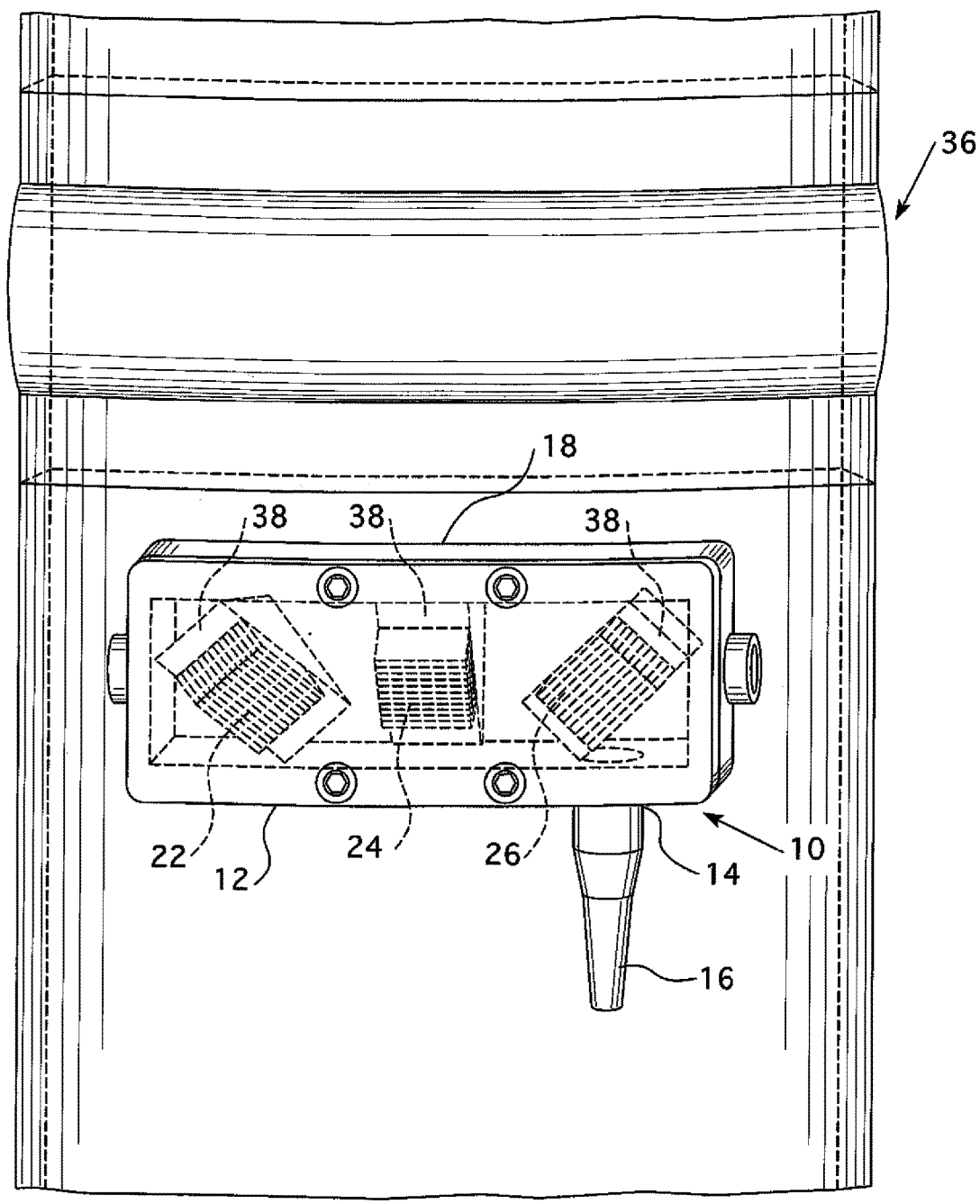
FIG. 6 shows the transducer of FIG. 1 positioned over a weld.

FIG. 4 shows the phased array transducer assembly 10 positioned adjacent a weld volume, i.e., the weldment 34 and the heat effected zone 30. The base metal 32 of the pipe 36 is shown on either side of the weld volume. As previously mentioned FIG. 5 shows the face 18 of the transducer assembly 10 being closely matched with the curvature of the pipe 36. FIG. 6 shows the view of the transducer assembly 10, shown in FIG. 1, adjacent the pipe 36.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. An ultrasonic phased array transducer assembly comprising a single ultrasonic probe housing in which a plurality of phased array transducers, respectively comprised of a plurality of transducer subassemblies, are mounted with at least two of the phased array transducers respectively positioned at a skewed angle relative to a leading face of the probe housing and all of the phased array transducers are mounted at skewed angles to each other, with each of the transducer subassemblies in the respective phased array transducers mounted on a common composite wedge within the housing.

2. The ultrasonic phased array transducer assembly of claim 1 wherein the probe housing includes a contoured face to substantially match a surface of a pipe to be examined.

3. The ultrasonic phased array transducer assembly of claim 2 wherein the pipe is a jet pump riser pipe in a boiling water reactor.

4. The ultrasonic phased array transducer assembly of claim 1 wherein each of the phased array transducers has a conductor with each of the conductors tethered together into a single cable assembly which exits the probe housing at a single port.

5. The ultrasonic phased array transducer assembly of claim 1 wherein the ultrasonic phased array transducer assembly includes at least one mounting hole or feature for gimbal attachments.

6. The ultrasonic phased array transducer assembly of claim 1 wherein the plurality of phased array transducer assemblies comprise three or more phased array transducer assemblies.

7. The ultrasonic phased array transducer assembly of claim 6 wherein the at least two phased array transducer assemblies that are positioned at skewed angles relative to the leading face are mounted at substantially a reciprocal angle to each other.

8. The ultrasonic phased array transducer assembly of claim 7 wherein the third phased array transducer is mounted perpendicular to a weld surface.

9. The ultrasonic phased array transducer assembly of claim 8 wherein the third phased array transducer is mounted between the at least two phased array transducers that are mounted at the skewed angles relative to the leading face.

10. A method of inspecting a jet pump riser pipe in a boiling water nuclear reactor, the reactor having at least one jet pump riser pipe, with each riser pipe having at least one welded attachment such as a riser brace, the method comprising:

positioning at least one ultrasonic phased array probe housing adjacent to a surface of the riser pipe wherein a front leading face of the probe assembly is positioned adjacent to a weld to be inspected, the probe housing at least partially enclosing a plurality of phased array transducers respectively comprising a plurality of transducer subassemblies;

scanning the jet pump riser pipe with at least one ultrasonic phased array probe so that a scanned range of an ultrasonic beam emitted by the ultrasonic phased array probe comprises an area extending from a weld toe down the pipe and extends from a scan surface down at least partially towards an opposing surface of the pipe; and wherein the ultrasonic phased array probe housing includes at least two independent phased array subassemblies mounted on composite wedges and set at skewed angles relative to each other and to a front leading face of the probe housing, with each of the transducer subassemblies in the respective phased array transducers mounted on a common composite wedge within the housing.

11. A method in accordance with claim 10 wherein the scan has a number of angles and the scanning angles are capable of detecting flaws oriented axially and circumferentially relative to the pipe weld.

* * * * *